(12) United States Patent
Jamali

(10) Patent No.: US 8,419,739 B2
(45) Date of Patent: Apr. 16, 2013

(54) METHOD AND APPARATUS FOR ALLOGRAFT DISC TRANSPLANTATION

(76) Inventor: Amir A. Jamali, Sacramento, CA (US)

( * ) Notice: Subject to any disclaimer, the term of this patent is extended or adjusted under 35 U.S.C. 154(b) by 78 days.

(21) Appl. No.: 12/862,535

(22) Filed: Aug. 24, 2010

(65) Prior Publication Data

US 2011/0046628 A1   Feb. 24, 2011

Related U.S. Application Data

(60) Provisional application No. 61/274,899, filed on Aug. 24, 2009.

(51) Int. Cl.
*A61F 5/00* (2006.01)
(52) U.S. Cl.
USPC .............................................. 606/87; 606/246
(58) Field of Classification Search ............. 606/87–89, 606/105, 86 A, 86 R, 84, 246; 623/17.11–17.16
See application file for complete search history.

(56) References Cited

U.S. PATENT DOCUMENTS

| | | | |
|---|---|---|---|
| 5,258,043 A | 11/1993 | Stone | |
| 5,417,695 A * | 5/1995 | Axelson, Jr. | .................... 606/89 |
| 5,423,823 A | 6/1995 | Schmieding | |
| 5,514,180 A | 5/1996 | Heggeness | |
| 5,545,229 A | 8/1996 | Parsons | |
| 5,645,597 A | 7/1997 | Krapiva | |
| 5,782,835 A | 7/1998 | Hart | |
| 5,824,078 A | 10/1998 | Nelson | |
| 5,919,196 A | 7/1999 | Bobic et al. | |
| 5,928,284 A | 7/1999 | Mehdizadeh | |
| 6,344,058 B1 | 2/2002 | Ferree | |
| 6,358,253 B1 | 3/2002 | Torrie | |
| 6,488,033 B1 | 12/2002 | Cerundolo | |
| 6,579,321 B1 | 6/2003 | Gordon | |
| 6,591,581 B2 | 7/2003 | Schmieding | |
| 6,994,727 B2 | 2/2006 | Khandkar | |
| 6,997,954 B2 | 2/2006 | Zubok | |
| 7,018,412 B2 | 3/2006 | Ferreira | |
| 7,169,183 B2 | 1/2007 | Liu | |
| 7,264,634 B2 | 9/2007 | Schmieding | |
| 7,309,358 B2 | 12/2007 | Berry | |
| 7,445,635 B2 | 11/2008 | Fallin | |

(Continued)

FOREIGN PATENT DOCUMENTS

| | | |
|---|---|---|
| WO | WO03066120 | 8/2003 |
| WO | WO03079939 | 10/2003 |

(Continued)

OTHER PUBLICATIONS

Ricci, J.A.; Stewart, W.F.; Chee, E.; Leotta, C.; Foley, K.; Hochberg, M.C. "Back pain exacerbations and lost productive time costs in United States workers." Spine. 2006; 31(26): 3052-3060.

(Continued)

*Primary Examiner* — Nicholas Woodall
*Assistant Examiner* — Melissa A Hall
(74) *Attorney, Agent, or Firm* — Craig M. Stainbrook; Stainbrook & Stainbrook, LLP

(57) ABSTRACT

A method and apparatus for the preparation and implantation of an osteochondral allograft of the intervertebral disc with the adjacent bone segments prepared in a matched fashion to allow for press-fit of the grafts into the recipient vertebral bodies to increase the mechanical fixation of the grafts to the host.

9 Claims, 20 Drawing Sheets

U.S. PATENT DOCUMENTS

| | | |
|---|---|---|
| 2005/0043800 A1 | 2/2005 | Paul |
| 2005/0102029 A1 | 5/2005 | Blain |
| 2006/0276900 A1 | 12/2006 | Carpenter |
| 2007/0135918 A1 | 6/2007 | Malinin |
| 2008/0161924 A1 | 7/2008 | Viker |
| 2008/0255623 A1 | 10/2008 | Steiner |

FOREIGN PATENT DOCUMENTS

| | | |
|---|---|---|
| WO | WO2007016247 | 2/2007 |
| WO | WO2007142744 | 12/2007 |
| WO | WO2008076181 | 6/2008 |

OTHER PUBLICATIONS

Luk, K.D.; Ruan, D.K.; Lu, D.S.; Fei, Z.Q. "Fresh frozen intervertebral disc allografting in a bipedal animal model." Spine. 2003; 28(9): 864-869; discussion 870.

Luk, K.D.; Ruan, D.K.; Chow, D.H.; Leong, J.C. "Intervertebral disc autografting in a bipedal animal model." Clin Orthop Relat Res. 1997 (337): 13-26.

Luk, K.D.; Ruan, D.K. "Intervertebral disc transplantation: a biological approach to motion preservation." Eur Spine J. 2008; 17 Suppl 4: 504-510.

Ruan, D.; He, Q., Ding, Y.; Hou, L.; Li, J.; Luk, K.D. Intervertebral disc transplantation in the treatment of degenerative spine disease: a preliminary study. Lancet 2007; 369(9566): 993-999.

Stewart, W.F.; Ricci, J.A.; Chee, E.; Morganstein, D.; Lipton, R. Lost productive time and cost due to common pain conditions in the US workforce. JAMA. 2003; 290(18): 2443-2454.

Guo, H.R.; Tanaka, S.; Halperin, W.E.; Cameron, L.L. Back pain prevalence in US industry and estimates of lost workdays. Am J Public Health. 1999; 89(7): 1029-1035.

Katz, J.N. Lumbar disc disorders and low-back pain; socioeconomic factors and consequences. J Bone Joint Surg Am. 2006; 88 Suppl 2:21-24.

From the Centers for Disease Control and Prevention. Prevalence of disabilities and associated health conditions among adults—United States, 1999. JAMA 2001; 285(12): 1571-1572.

Freburger, J.K.; Holmes, G.M.; Agans, R.P.; Jackman, A.M.; Darter, J.D.; Wallace, A.S.; Castel, L.D.; Kalsbeek, W.D., Casey, T.S. The rising prevalence of chronic low back pain. Arch Intern Med. 2009; 169(3): 251-258.

\* cited by examiner

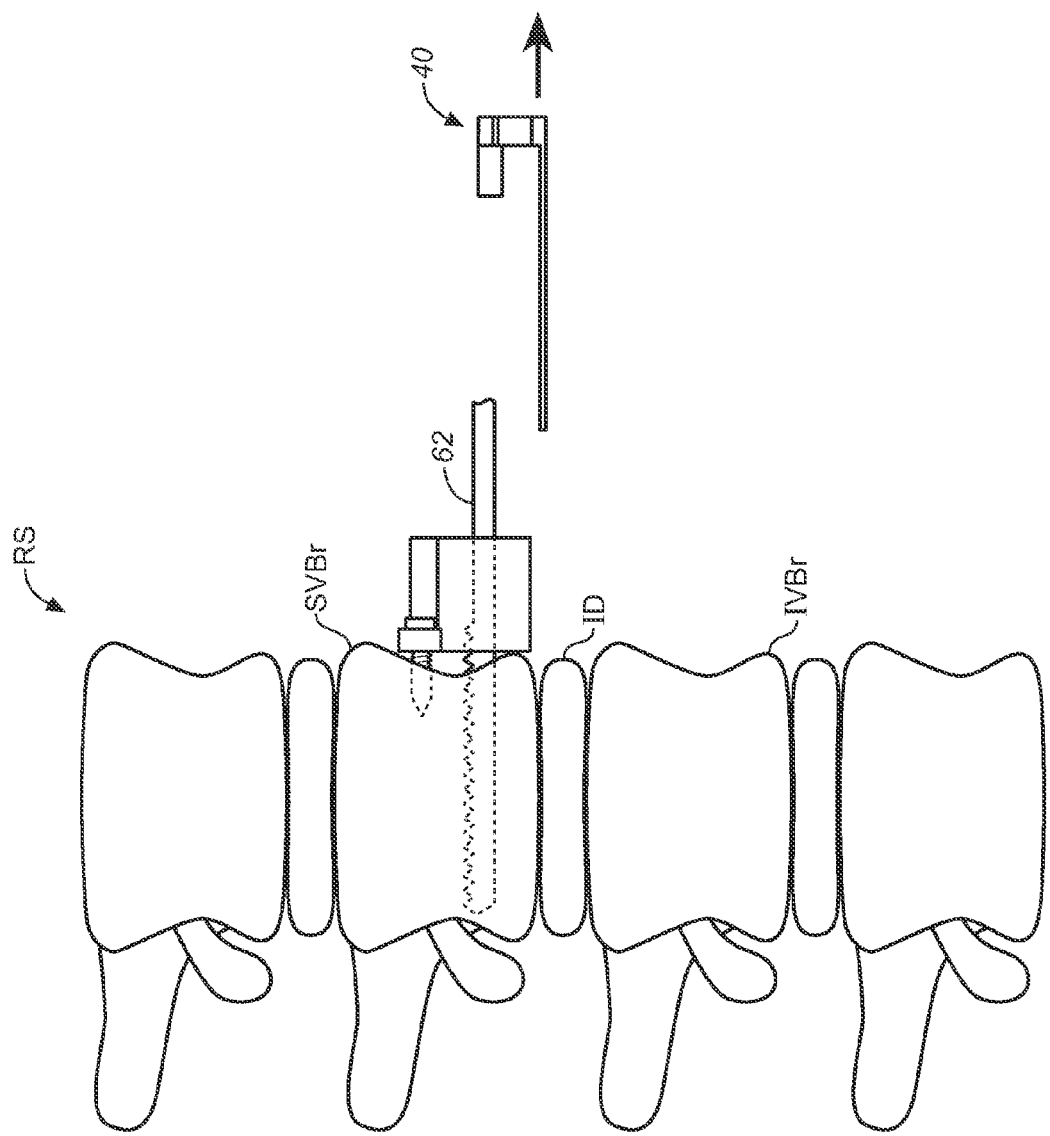

METHOD AND APPARATUS FOR ALLOGRAFT DISC TRANSPLANTATION

CROSS REFERENCES TO RELATED APPLICATIONS

The present application claims the benefit of U.S. Provisional Patent Application Ser. No. 61/274,899, filed Aug. 24, 2009.

STATEMENT REGARDING FEDERALLY SPONSORED RESEARCH OR DEVELOPMENT

Not applicable.

NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

SEQUENCE LISTING

Not applicable.

BACKGROUND OF THE INVENTION

1. Field of the Invention

The present invention relates generally to methods of performing surgical bone transplants. More particularly, the present invention relates to techniques by which donor allograft vertebral bones and intervertebral discs may be transplanted into a recipient patient to treat degenerative disc disease of the cervical, thoracic, and/or lumbar spine.

2. Background Discussion

Osteochondral allografts have a long history of clinical success in the treatment of articular cartilage defects in the knee, shoulder, hip, and ankle The principal advantage of the technique over all other techniques of cartilage restoration is the maintenance of an intact interface between the bone and cartilage of the graft and the preservation of the cartilage architecture; the allograft bone is placed in such a way that it heals to the bone of the recipient.

Spinal degenerative disc disease is the second most common cause of disability and a major cause of lost work days in the United States. (Morbidity and Mortality Weekly Report. 2001; 50:94-97) The economic impact of this disease is staggering, accounting for an estimated 149 million days of lost work per year due to low back pain in the United States (H.R. Guo, et al., Am J Public Health, 1999; 89(7): 1029-1035). The estimated cost is between $100 billion and $200 billion per year, mainly due to decreased productivity.(Katz, JN. Bone Joint Surg (Am), 2006; 88 Suppl. 2:21-24). The strategies for the treatment of degenerative disc disease in most cases do not involve surgery. However, should such treatment fail, surgical treatment consisting of nerve decompression and discectomy may be indicated. In more severe cases of disc degeneration or in cases associated with deformity, spinal arthrodesis (fusion) or disc replacement has been advocated. The advantages of fusion are the high rate of clinical success in pain relief and in the correction of deformity. The disadvantage is in the risk of adjacent segment degeneration.

Disc replacement has been developed over the past 20 years and has recently been approved by the United States Food and Drug Administration. The long term results of this procedure are unknown. Furthermore, as the procedure is performed through the anterior approach, revision for failure is an exceedingly dangerous procedure. Additionally, the generation of particular wear debris adjacent to the great vessels may bring up some catastrophic complications.

Spinal discs are similar to articular cartilage in their composition from collagen, proteoglycans, and water. As such, disc allograft transplants have been performed with some early success in the cervical spine as published by Luk, K.D., et al (Spine, 2003; 28(9): 864-869). The present invention applies principles learned from fresh osteochondral allograft procedures to the treatment of spinal disc degenerative disease. The objective of the procedure is to maintain segmental motion with a fresh or frozen allograft bone-disc composite, taking advantage of the avascular properties of the disc and achieving rigid fixation to the host vertebral bodies on both sides of the allograft.

BRIEF SUMMARY OF THE INVENTION

The present invention includes a method and apparatus for the preparation, transplantation, and fixation of fresh osteochondral allografts of the vertebral bones and the intervertebral discs for the treatment of degenerative disc disease of the cervical, thoracic, or lumbar spine of humans and other mammals. In its most general aspect, the inventive apparatus includes a first and second bone cutting assembly, the first bone cutting assembly employed to prepare a contoured cavity in a recipient spinal segment to receive a bone/disc allograft, the second cutting assembly to prepare the bone/disc combination allograft to tightly fit into the previously prepared contoured cavity. Using the inventive apparatus and methods, a precisely machined allograft hybrid comprising a superior vertebral body, an intervertebral disc, and an inferior vertebral body is prepared while maintaining the allograft disc in its pristine condition without any penetration of its annulus fibrosis.

Additionally, the invention includes a method for the preparation of the recipient diseased disc and adjacent vertebral bodies to receive the allograft hybrid tissue. This is facilitated by precisely shaping and sizing the bone segments of the donor and recipient to match so as to facilitate provide for a press fit fixation of the bone and to allow rapid healing between the donor and recipient bone. The intervertebral disc is in many ways an ideal tissue for transplantation due to its limited vascular supply. Furthermore since the transplant is denervated, the inventive method provides an excellent treatment for low back pain caused by degenerative disc disease and one that avoids the complications associated with intervertebral fusion and total disc transplantation.

The novel features characteristic of the invention, as to structure, composition, organization, and method of operation, together with further objects and advantages thereof will be better understood from the following description, considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. Those skilled in the art will appreciate that the conception, upon which this disclosure is based may readily be used as a basis for designing other structures, methods, and systems for carrying out the several purposes of the present invention. The claims should be understood to include such equivalent constructions as far as they do not depart from the spirit and scope of the present invention.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein:

FIG. 2C is a side view in elevation showing how the disc measurement stylus is removed after cutting has commenced;

DETAILED DESCRIPTION OF THE INVENTION

Figure 1A:
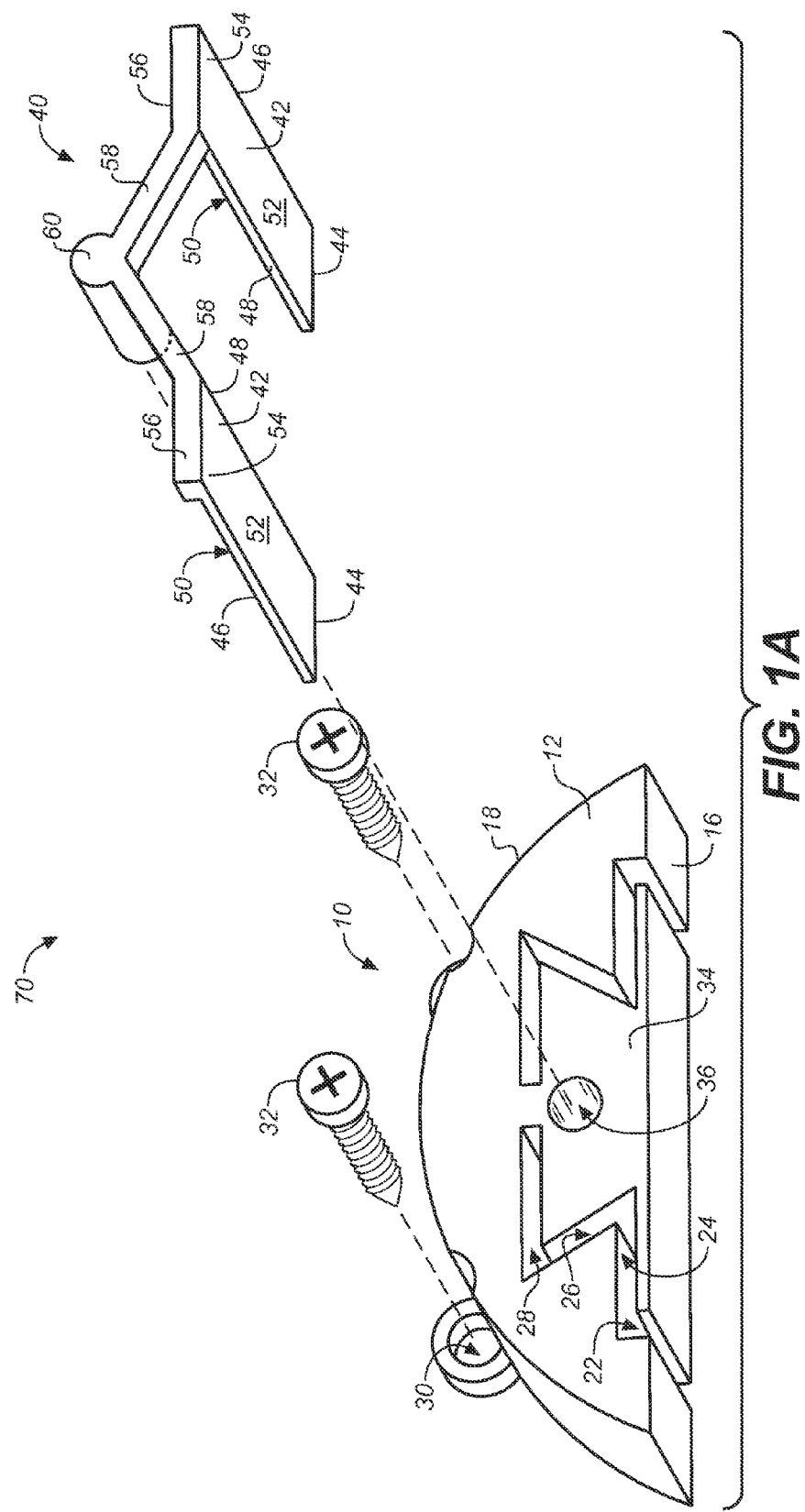
FIG. 1A is a lower front exploded perspective view of the cutting jig and disc measurement stylus of the present invention.
Figure 1B:
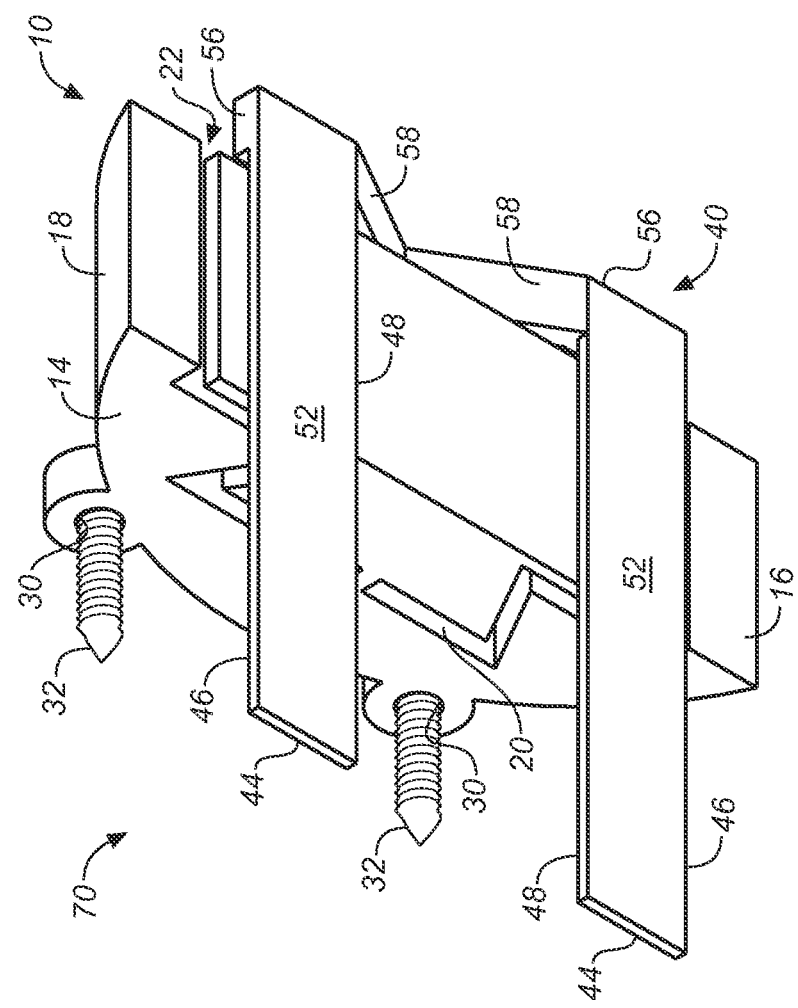
FIG. 1B is a lower rear perspective view of the assembled cutting jig and disc measurement stylus of FIG. 1A, showing the stylus inserted into the cutting jig.

Referring first to FIGS. 1A and 1B, there is shown in perspective view a first bone cutting assembly 70 of the present invention. This assembly is adapted for use in preparing a contoured cavity in a recipient spinal segment for transplantation of a combination bone/disc allograft harvested from a donor spinal segment. These views show that the first cutting assembly includes a cutting guide (or jig) 10, which has a front side 12, a rear side 14, a generally planar bottom side 16, an arcuate upper side 18, and cutting slots 20 to guide the exact path of a cutting device, such as a saw blade or cutting burr. In a preferred embodiment of the invention, the cutting slots include an initial short vertical segment 22 which opens to and through the bottom side of the jig. This "opening slot" is followed by a longer centrally directed first horizontal segment 24, followed by an oblique segment 26 directed away from center, and finally a centrally directed second horizontal segment 28. In this way, a precise dovetail pattern is cut into both the donor and recipient vertebral bodies.

Two screw holes 30 are disposed on the superior aspect of the top side of the jig for passing screws 32 to secure the jig to the vertebral body during the preparation process. In the central portion 34 of the jig, a cylindrical hole 36 is provided for insertion of an indexing element of a disc measurement stylus, such as a cylindrical indexing peg.

The disc measurement stylus 40 of the present invention. The stylus consists of two spaced apart and generally parallel horizontal blades 42 that slide into the annulus fibrosis of the diseased disc on the surface of the bone end plate and establish the depth of bone removal from the vertebral bodies such that the neural elements are protected posteriorly. The blades each include a leading edge 44, an outer spine 46, an inner edge 48, an upper surface 50, a lower surface 52, a heel portion 54, and a bolster 56. The bolsters are connected with upwardly angling elements 58 of equal length which converge at a vertex to form a central cylindrical peg 60, which fits within the cylindrical hole 36 of the cutting jig.

FIG. 1B is a lower rear perspective view showing the cutting jig with the attached disc measurement stylus with its blades 42 and its central cylindrical peg 60 placed within the cylindrical indexing hole 36 of the cutting jig 10. These two elements—the cutting jig and attached disc measurement stylus—comprise the apparatus adapted for performing the first phase of the osteochondral allograft procedure of the present invention, namely, preparation of the transplant site in the recipient patient spinal segment. For simplification these assembled bone and disc cutting elements are variously referred to herein as either the first cutting assembly or "the recipient bone cutting assembly" 70.

Figure 2A:
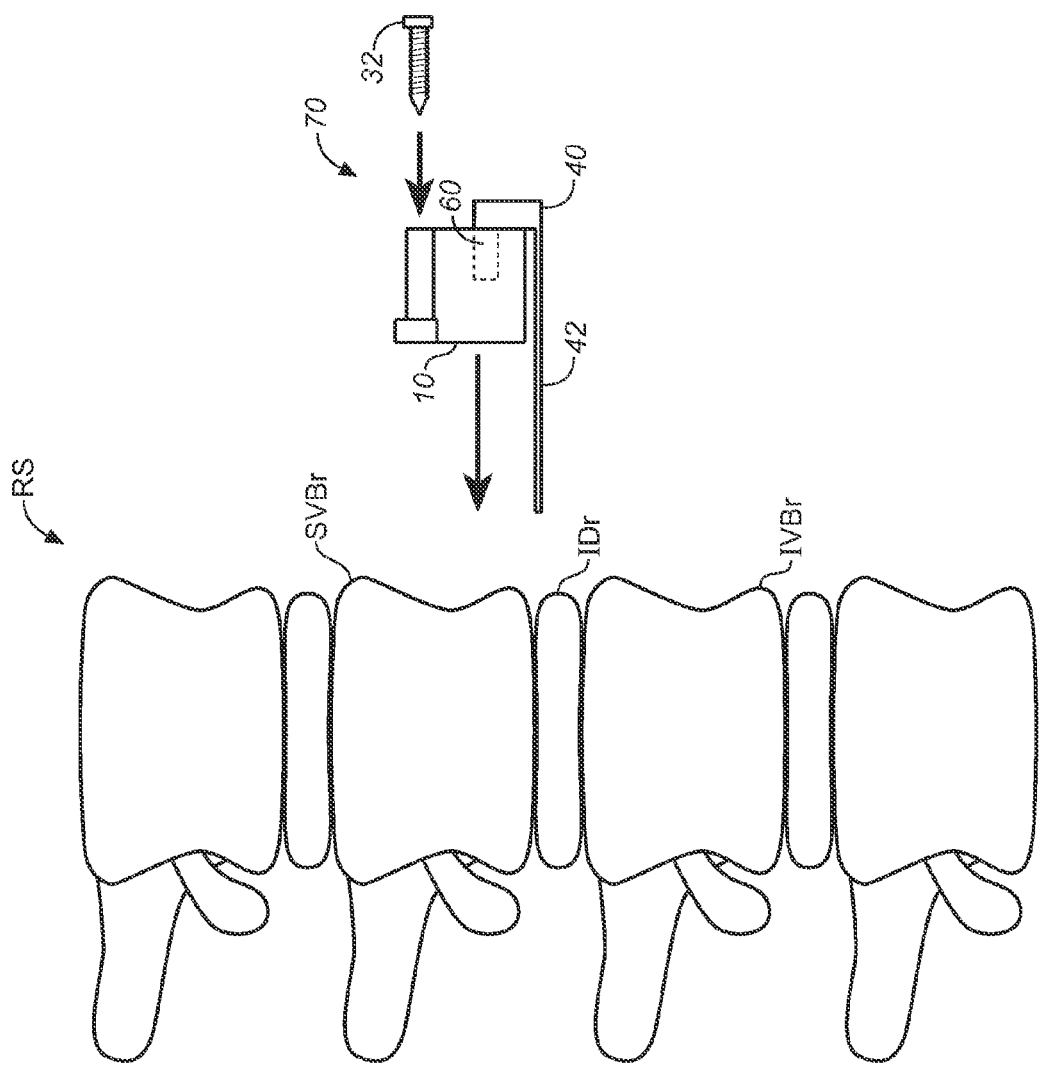
FIG. 2A is a side view in elevation showing a recipient lumbar spine with the cutting jig and disc measurement stylus of FIGS. 1A-1B poised for insertion and placement.

FIG. 2A, is a side view in elevation showing a recipient spinal segment RS with the cutting jig 10 and disc measurement stylus 40 of FIGS. 1A-1B poised for placement on the anterior aspect of the recipient spine. In this instance, the spinal segment is a portion of the lumbar spine. From this position the first of two recipient bone cutting processes will be carried out to define and create the space for placement of a donor osteochondral allograft. The cutting assembly is placed first at the superior vertebral body SVBr and the diseased intervertebral disc segment IDr. This view also shows the screws 32 positioned for insertion in the screw holes disposed on the superior portion of the top side of the cutting jig. The inferior vertebral body IVBr is not involved in the first cutting process.

Figure 2B:
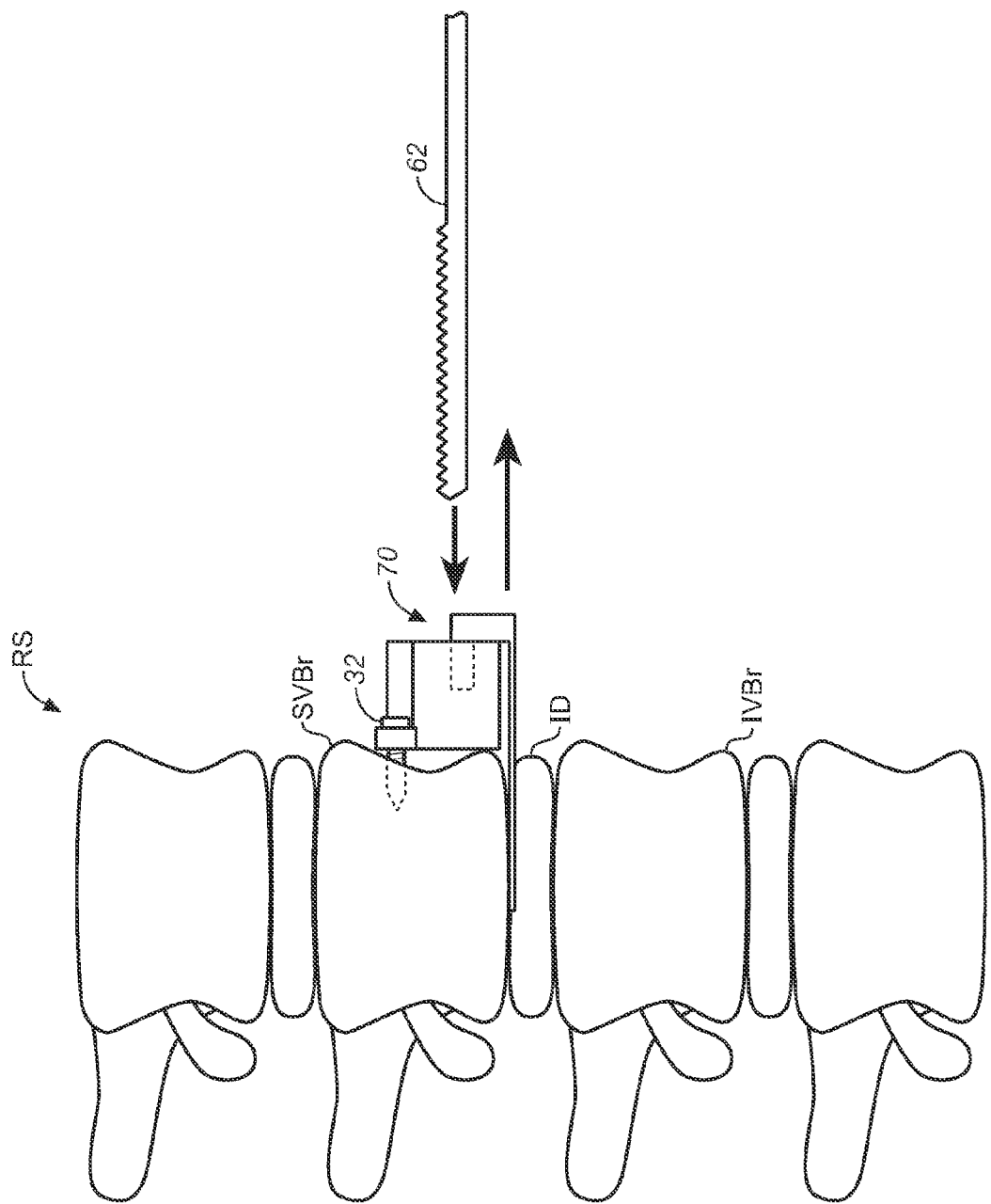
FIG. 2B is a side view in elevation of the recipient lumbar spine with the cutting jig and disc measurement stylus inserted in the intervertebral disc and the cutting jig screwed in place at the superior vertebral body of the diseased disc segment; the saw blade is shown poised for insertion in the jig to commence cutting.

FIG. 2B is a side view in elevation showing the first (recipient) cutting assembly 70 affixed to the recipient spine RS superior vertebral body SVBr with screws 32 threadably inserted into the superior end plate SEPr of the vertebral body and the disc measurement stylus 40 with its horizontally disposed blades 42 placed within the annulus fibrosis of the recipient's diseased disc in such a way as to protect the posterior neural elements. Once the cutting jig is secured by screws, the disc measurement stylus may be removed (see FIG. 2C). A cutting device, such as a cutting burr or saw blade 62, is then inserted into the cutting slots 20.

FIG. 2C shows how the disc measurement stylus 40 is removed from the annulus fibrosis when the cutting process commences.

After passage of the cutting device using the cutting slots of the cutting jig, the screws are unscrewed and the jig is removed from the superior vertebral body. The cut portion of the superior end plate may be removed at this time. Preferably, however, this removal may be deferred until completion of the second cutting process of the inferior vertebral body. The residual screw holes SHr remain (see FIGS. 3A-3B), as does the new contoured cavity defined within the superior vertebral body that is in continuity with the diseased disc space.

Figure 2D:
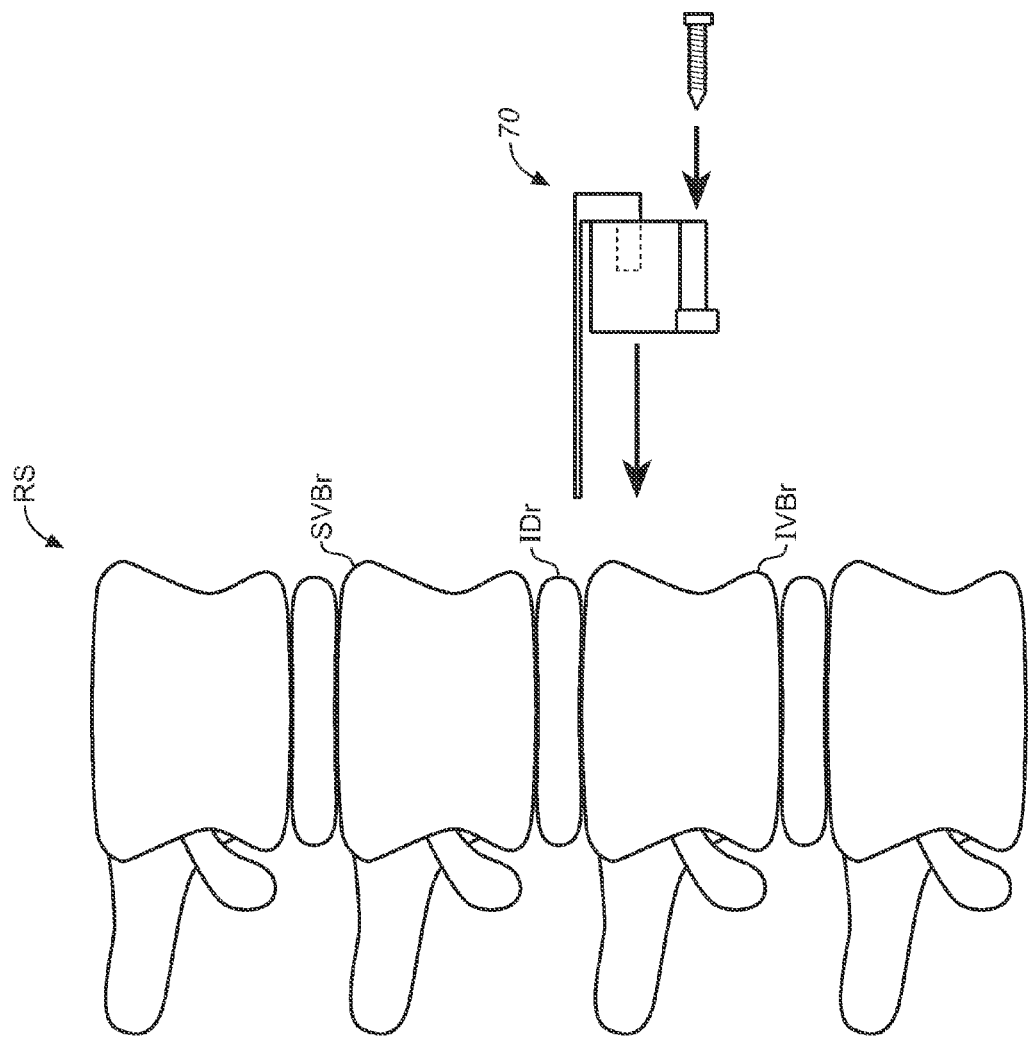
FIG. 2D shows the cutting jig removed from the superior vertebral body after cutting is completed, inverted, and then poised for placement on the inferior vertebral body.

FIG. 2D shows the first cutting assembly 70 inverted from its upright orientation in FIGS. 2A-2C and positioned for placement on the recipient lower vertebral body immediately under the intervertebral disc. In placing the cutting assembly for the second cutting process, and to effect the proper cavity contour, the edges of the opening slot in the bottom side of the cutting jig are aligned with the corresponding cut edges on the superior vertebral body end plate.

Figure 2E:
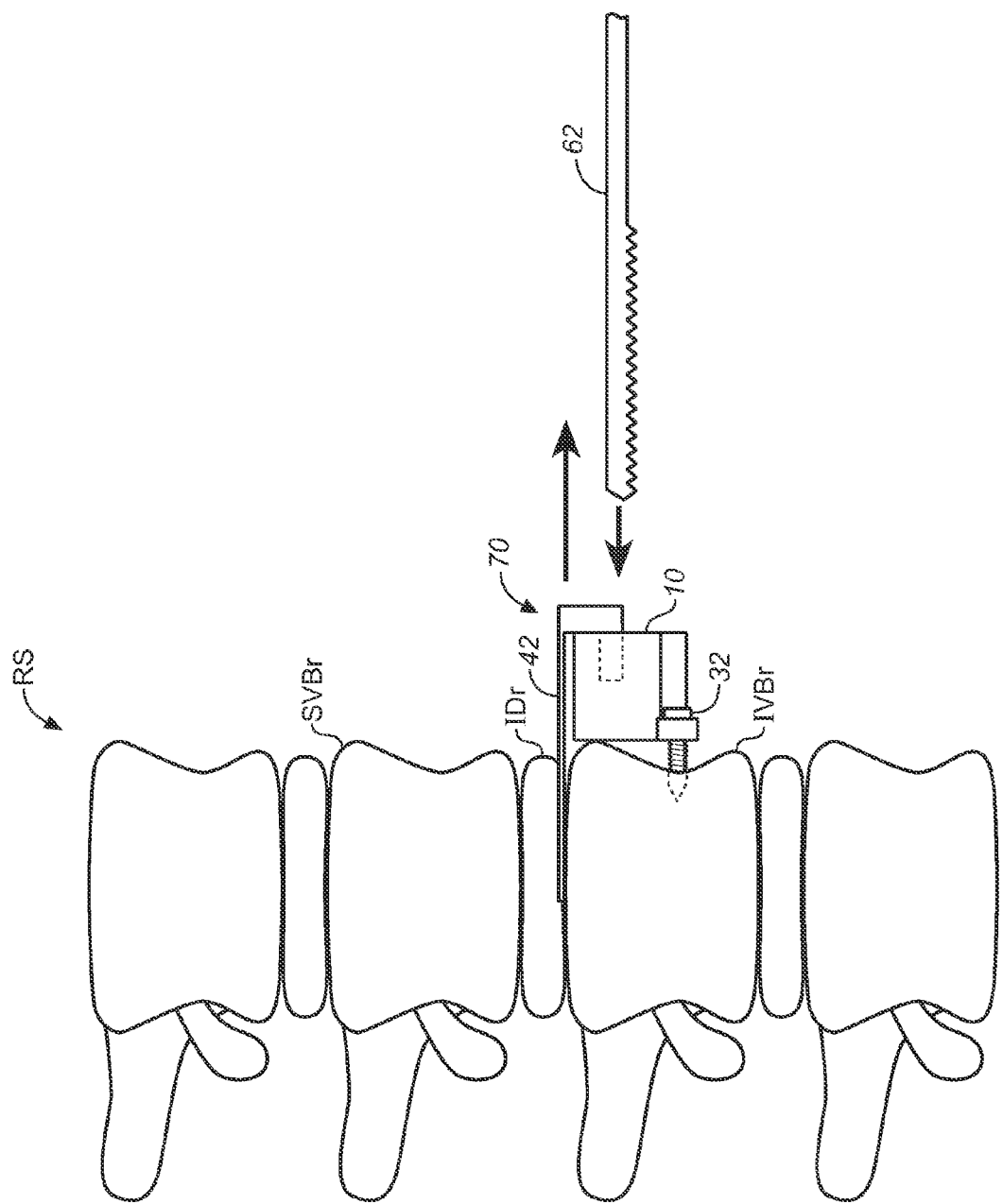
FIG. 2E shows placement of the cutting jig and disc measurement stylus on the inferior vertebral body with the saw poised to commence cutting.
Figure 2F:
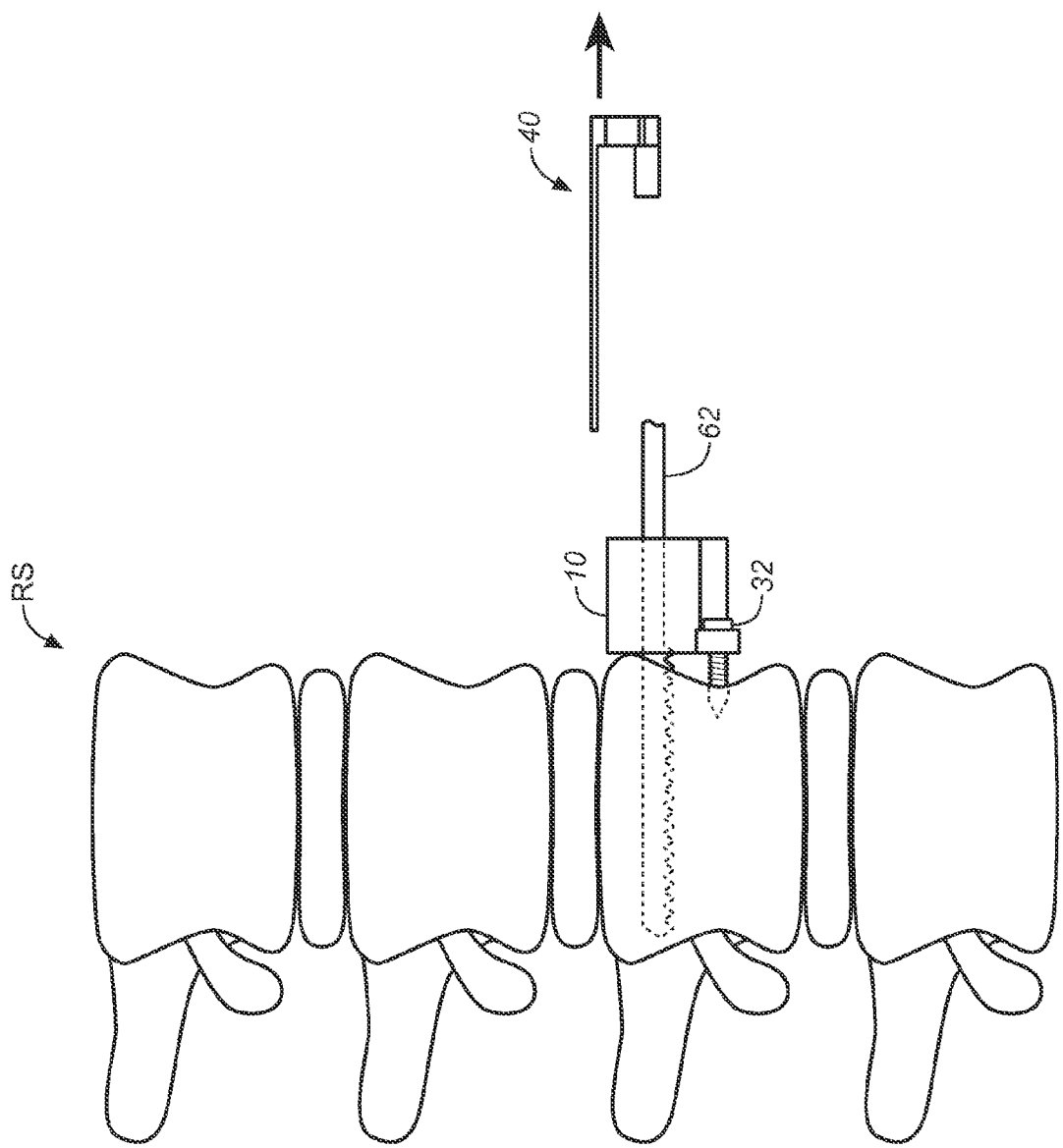
FIG. 2F shows removal of the disc measurement stylus after cutting of the inferior vertebral body of the diseased segment has commenced.

FIGS. 2E-2F show how the cutting process shown in FIGS. 2A-2C is repeated in a mirror fashion on the inferior vertebral body to complete the second cutting process. Again, the cutting assembly is fixed to the inferior vertebral body with screws and the disc measurement stylus with its horizontally disposed blades are placed within the inferior annulus fibrosis of the diseased disc. After passage of the cutting device through the slots of the cutting jig, the screws and the cutting jig are removed.

Figure 3B:
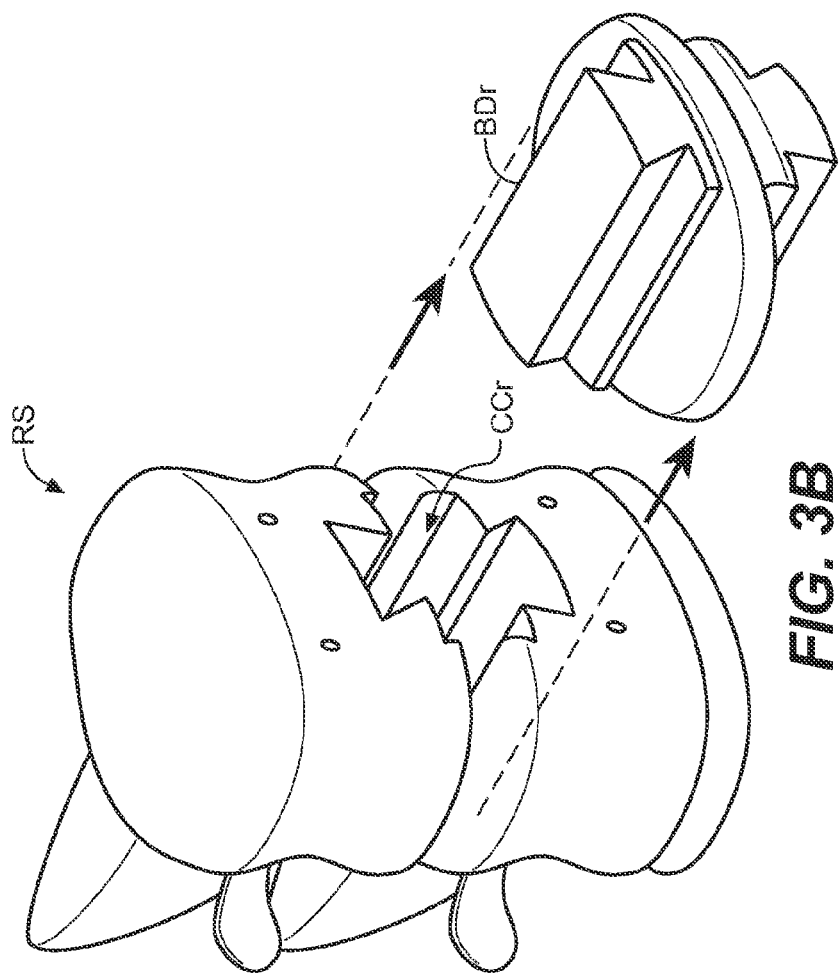
FIG. 3B is an upper perspective view showing the recipient lumbar spine after removal of the cutting jig, and the bone cuts from both the superior and inferior vertebral bodies, as well as the intervening disc.
Figure 3A:
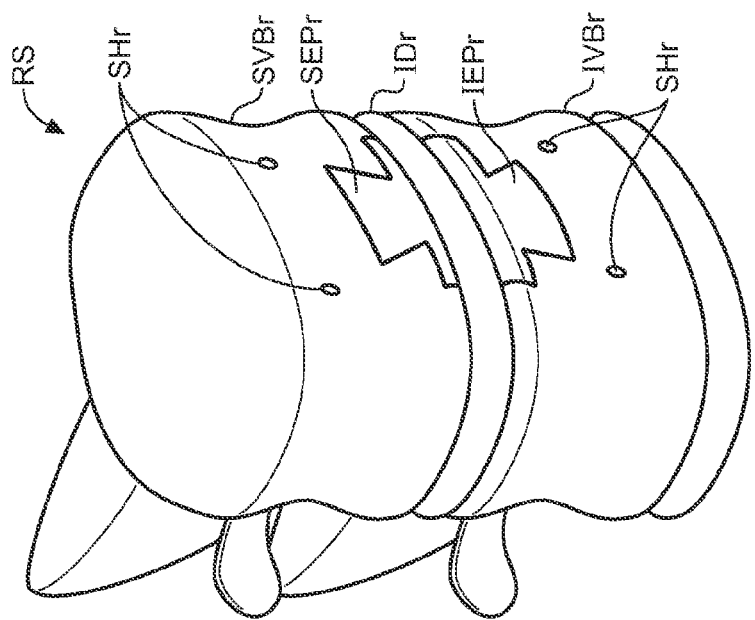
FIG. 3A is an upper perspective view showing the recipient lumbar spine after performance of saw cuts.

At this point the inferior end plate may be removed, as may the superior end plate, if not already removed. FIGS. 3A-3B show that when the cut portion BDr is removed after completion of the first and second (upper and lower) cutting process, the residual screw holes SHr in the inferior vertebral body remain as does the new contoured cavity CCr placed within the superior and inferior vertebral bodies and the intervertebral disc. (While the various bone tissues are not distinguished in the drawings, it should be understood that the tissue removed from the recipient may include compact bone, cancellous bone, and marrow.) Furthermore, the bone BDr can be removed en bloc after the cutting or in a piecemeal fashion using instruments well known to those skilled in the art. In particular in the posterior aspect of the vertebral body, great care is required to avoid inadvertent injury to the dural sac and thus manual preparation of the posterior most segment of CCr is required using instruments such as Kerrison rongeurs and pituitary rongeurs. At the end of this segment the CCr should extend all the way from the anterior to the posterior aspect of the vertebral body with the profile contoured to the cutting jig.

Figure 4:
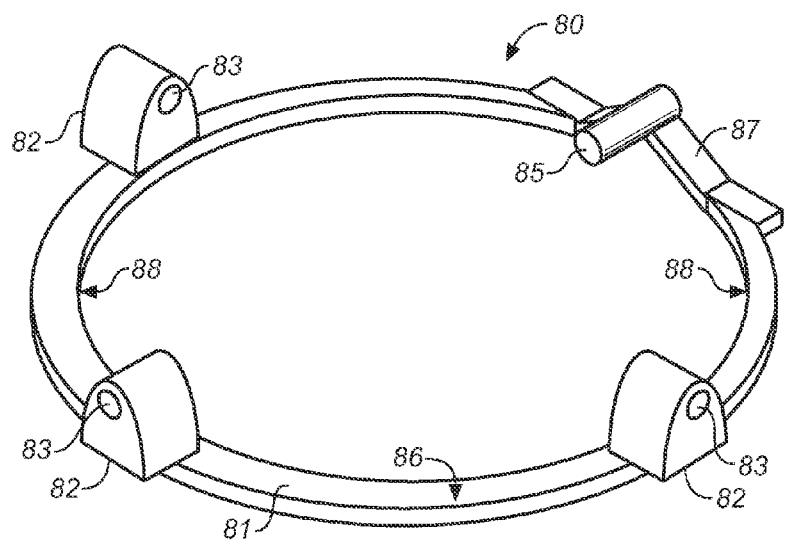
FIG. 4 is an upper rear perspective view of a donor alignment guide with a central peg installed for the positioning and placement of vertebral bodies and intervertebral discs into a recipient.
Figure 5:
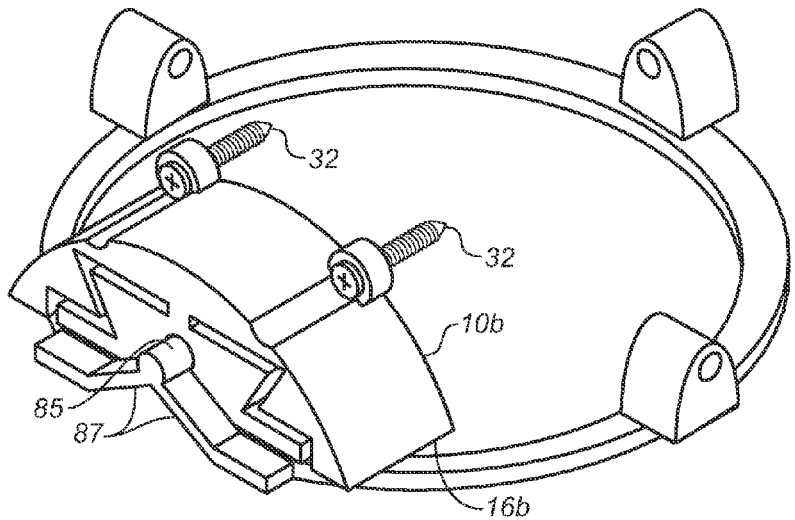
FIG. 5 is an upper front perspective view of the alignment guide of FIG. 4 showing the guide with a cutting jig installed over the central peg.
Figure 6A:
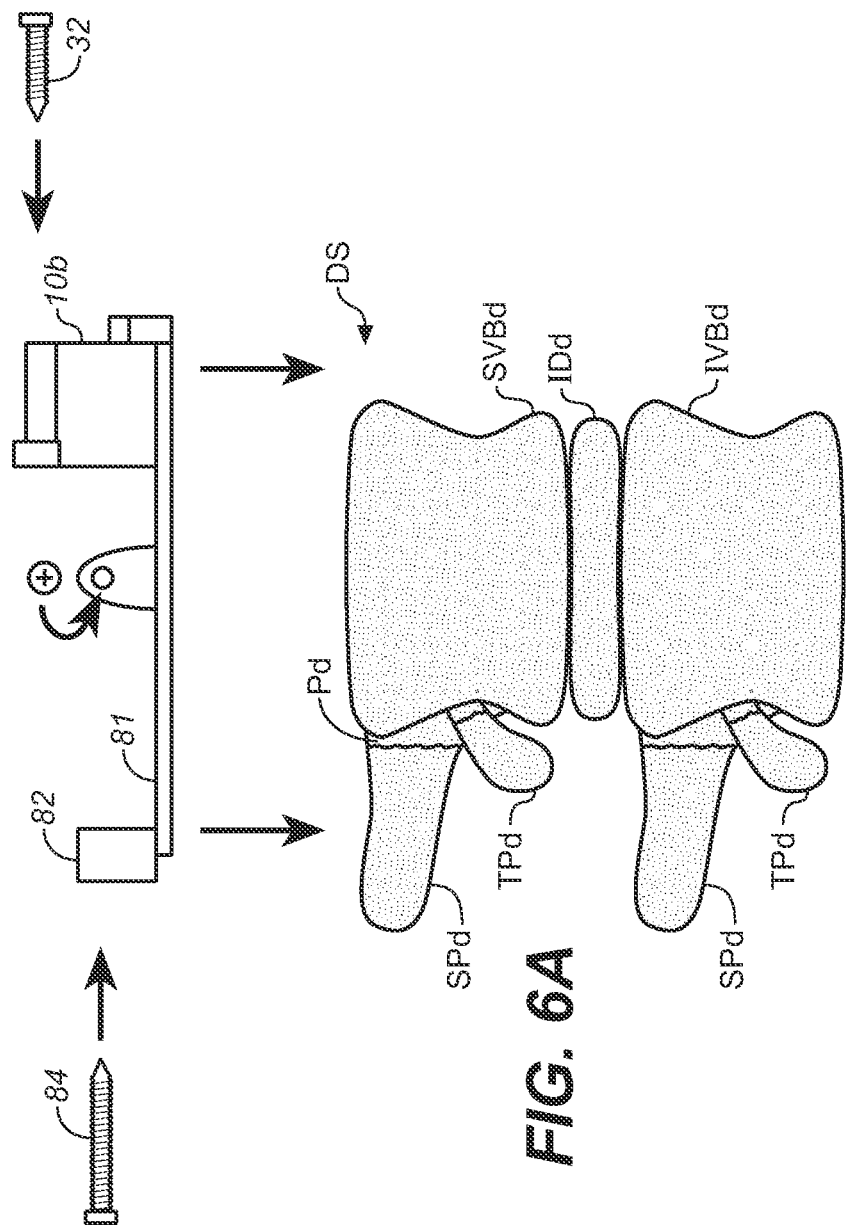
FIG. 6A is a side view in elevation showing the donor alignment guide of FIGS. 4-5 poised for placement on the superior vertebral body of a donor two level bone-disc-bone hybrid allograft.
Figure 6B:
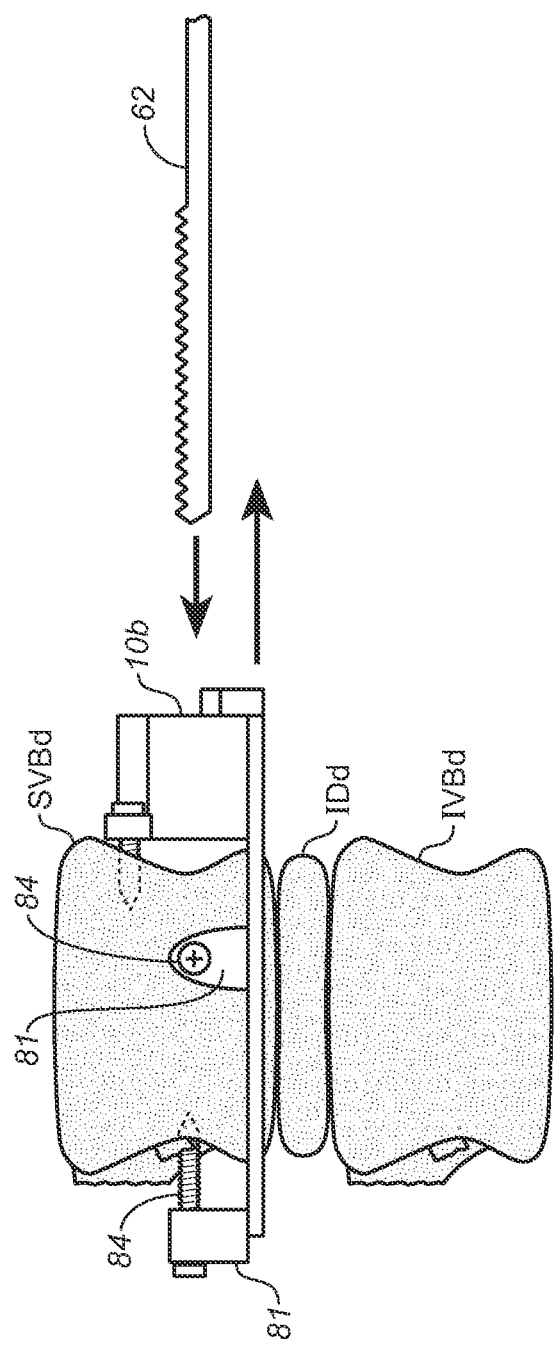
FIG. 6B is a side view in elevation showing the donor alignment guide placed on the donor allograft, which is typically positioned using visual or fluoroscopic guidance.
Figure 6C:
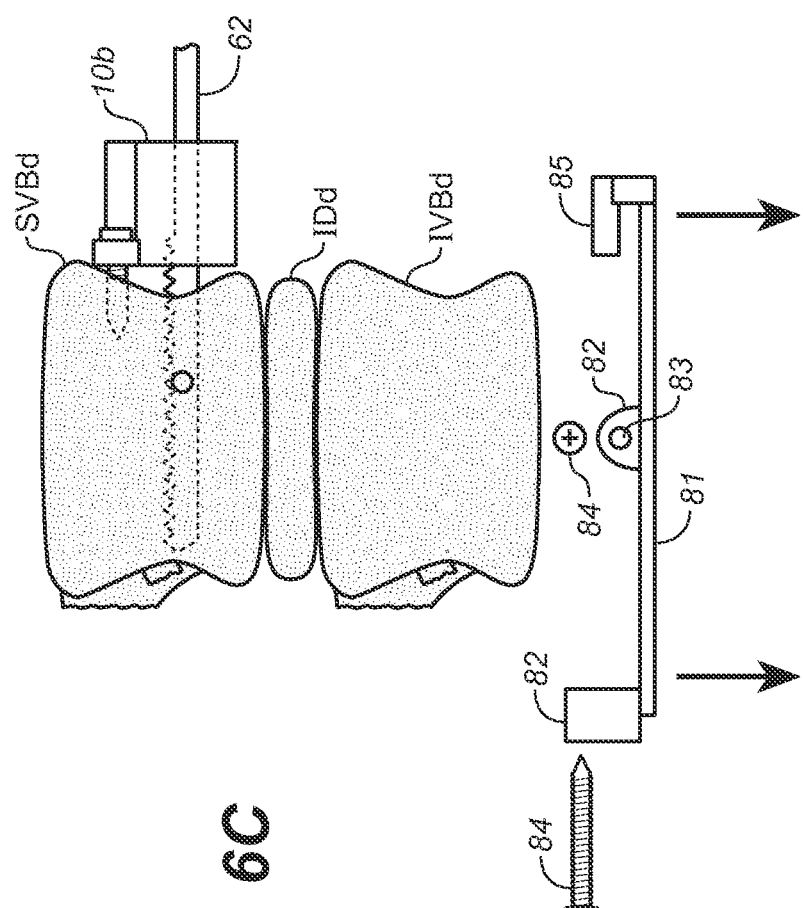
FIG. 6C is a side view in elevation showing the removal of the donor allograft alignment guide as cutting is commenced.
Figure 6D:
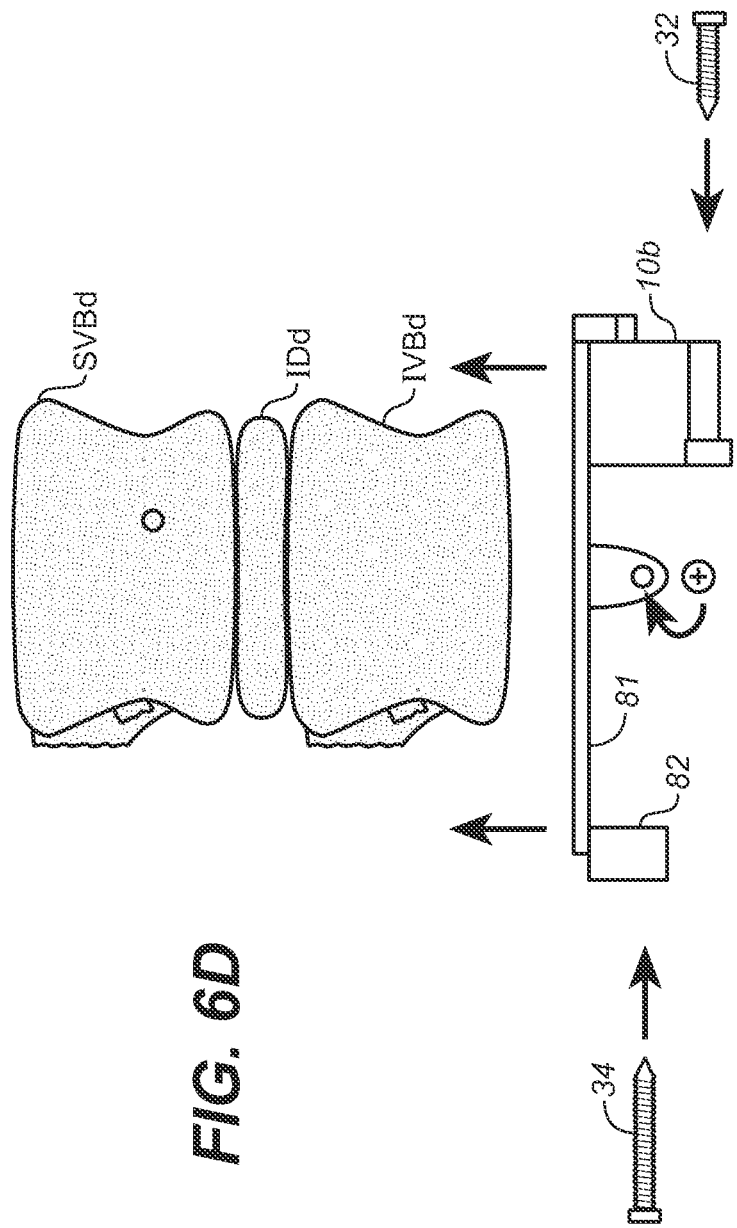
FIG. 6D is a side view in elevation showing the donor alignment guide inverted from its position in FIGS. 6A-6B for placement on the inferior vertebral body of the two level bone-disc-bone hybrid allograft.
Figure 6E:
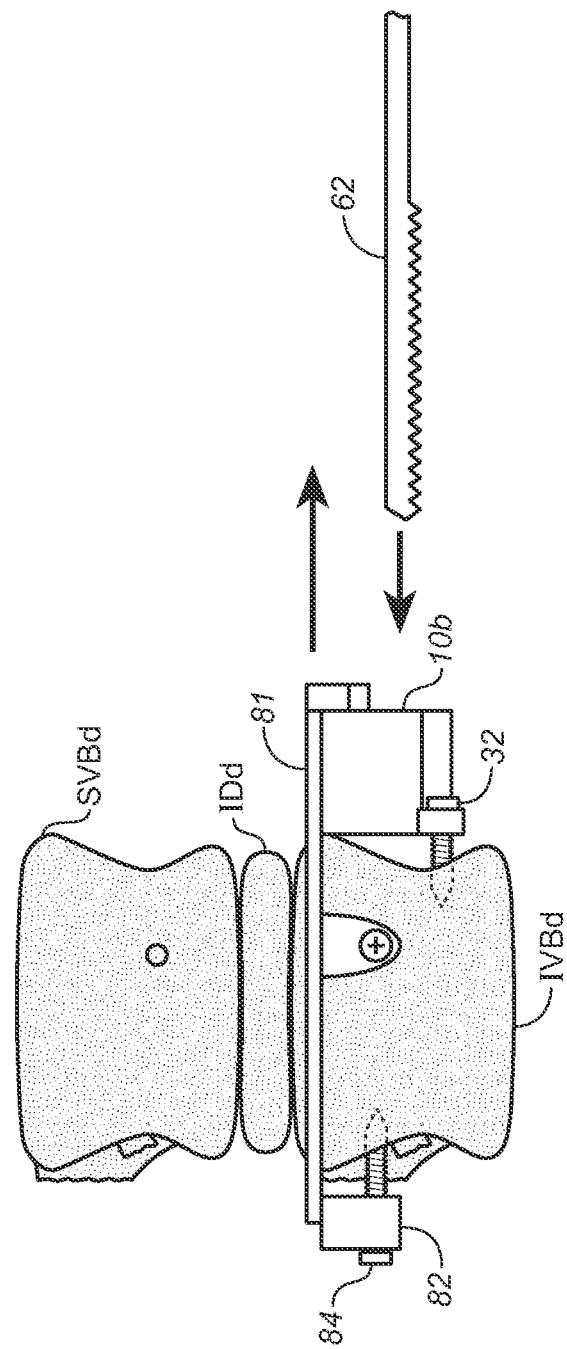
FIG. 6E shows placement of the donor alignment guide on the inferior vertebral body of the donor allograft.
Figure 6F:
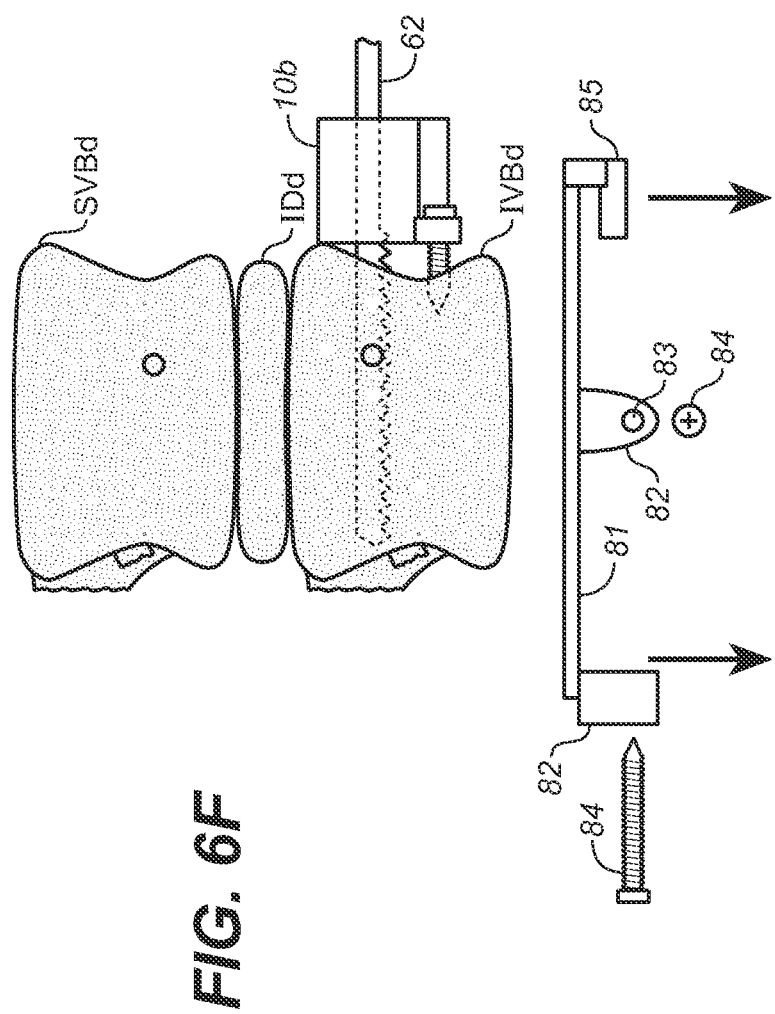
FIG. 6F shows removal of the alignment guide as cutting is commenced on the inferior vertebral body.

FIGS. 4 and 5 show the second bone cutting assembly employed in the present invention, this assembly including an alignment guide 80 employed for mounting a cutting jig 10b that matches the earlier described jig to create and harvest a combined bone/disc allograft from a donor which perfectly matches the contoured cavity of the recipient. The donor alignment guide includes an annulus 81 with a plurality of bosses 82 with screw holes 83 for affixing the guide to a donor spinal segment DS (see FIG. 6A et seq.) with suitable screws 84. A central cylindrical indexing peg 85 is disposed slightly above the upper surface 86 of the annulus so that a portion of the bottom side 16b of the cutting jig can be placed flush with that upper surface 86. Preferably, the indexing peg 85 is supported by either a vertical support or two angled supports 87, which generally match the supports 58 of the disc measurement stylus. As will be appreciated, the donor alignment guide is sized with an interior diameter 88 sufficiently large to permit placement over a donor spine segment DS after removal of both the spinous processes SPd and transverse processes TPd. The assembly comprising the donor alignment guide and the cutting jig may be referred to variously as either "the harvesting assembly" or simply the second cutting assembly.

As will be appreciated, in both the first and second cutting assemblies, the jig is described as including a hole or receptacle for insertion of an indexing element. However, the transposition of these elements will produce the same indexing function so as to ensure accurate placement of the jig on the stylus or on the alignment guide. Accordingly, the disc measurement stylus of the first cutting assembly may include an indexing hole and the jig an indexing peg; likewise, the donor alignment guide may include an indexing hole corresponding to an indexing peg disposed on the second cutting assembly jig body.

FIGS. 6A-7B illustrate the process of creating and harvesting the combined bone/disc allograft from a donor spine segment using the harvesting assembly. These views show that the donor spine segment is prepared by removing the spine segment from the donor and then removing all or a portion of the spinous processes SPd and transverse processes TPd from the superior vertebral body SVBd and the inferior vertebral body IVBd, preferably with cuts through the pedicle close to the dorsal aspect of each of the vertebral bodies. The annulus of the donor alignment guide is then placed over the superior vertebral body using fluoroscopic or visual landmarks and is affixed with screws. A cutting device is then inserted through the cutting slots of the jig and employed to make cuts that defines an outer contour of the combined bone/disc allograft that corresponds precisely with the interior edges and walls of the contoured cavity of the recipient. When the first cutting process on the superior vertebral body is completed, the donor alignment guide is removed and inverted for placement on the inferior vertebral body, and the process is then repeated in mirror fashion on the inferior vertebral body.

Figure 7B:
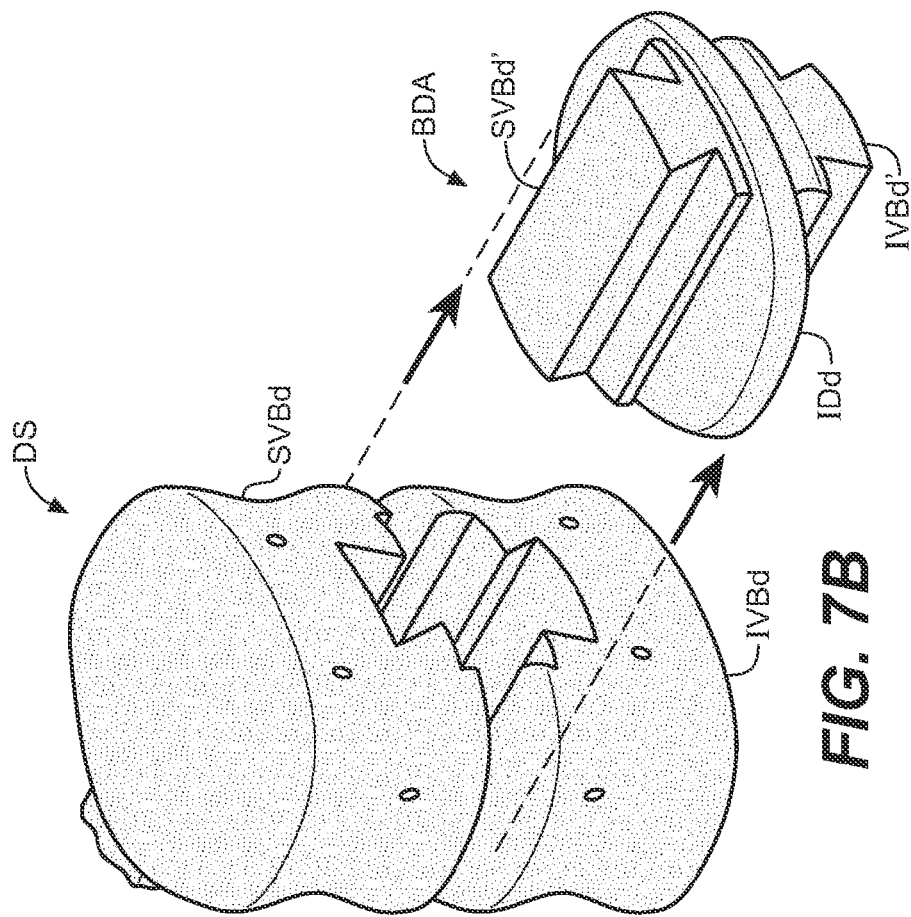
FIG. 7B is an upper rear perspective view showing the donor lumbar spine after removal of the bone cuts from both the superior and inferior vertebral bodies, as well as the intervening disc.
Figure 7A:
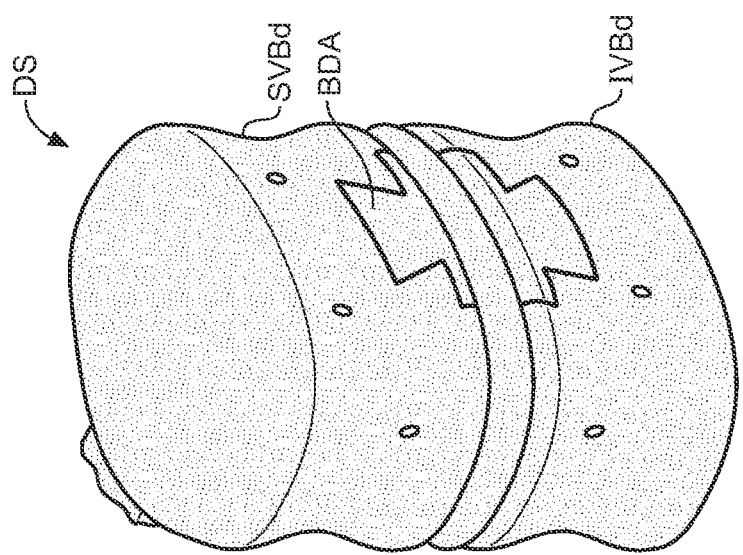
FIG. 7A is an upper rear perspective view showing the two level bone-disc-bone donor allograft after performance of saw cuts.

FIGS. 7A-7B show how the healthy combined bone/disc allograft BDA is removed after the cutting processes are completed. The combined bone/disc allograft includes the cut portion of the superior vertebral body SVBd', the intervening healthy intervertebral allograft disc IDd, and the cut portion of the inferior vertebral body IVBd'.

Figure 8B:
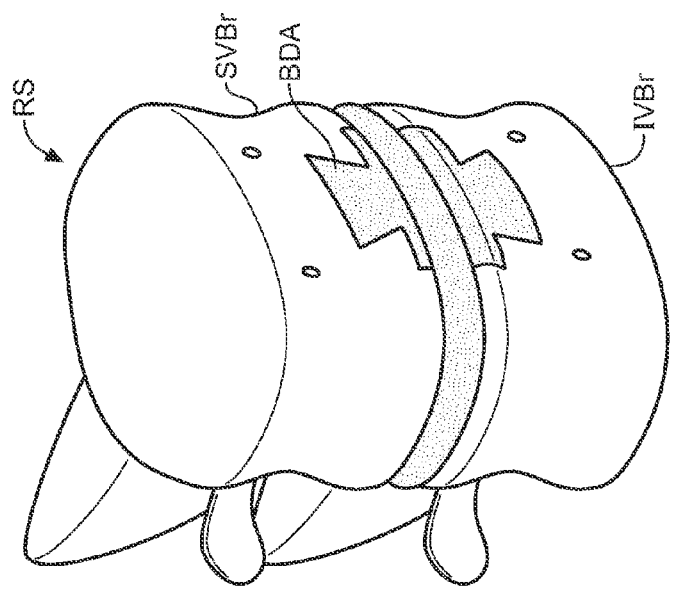
FIG. 8B is an upper rear perspective view showing the recipient spine after placement of the donor allograft.
Figure 8A:
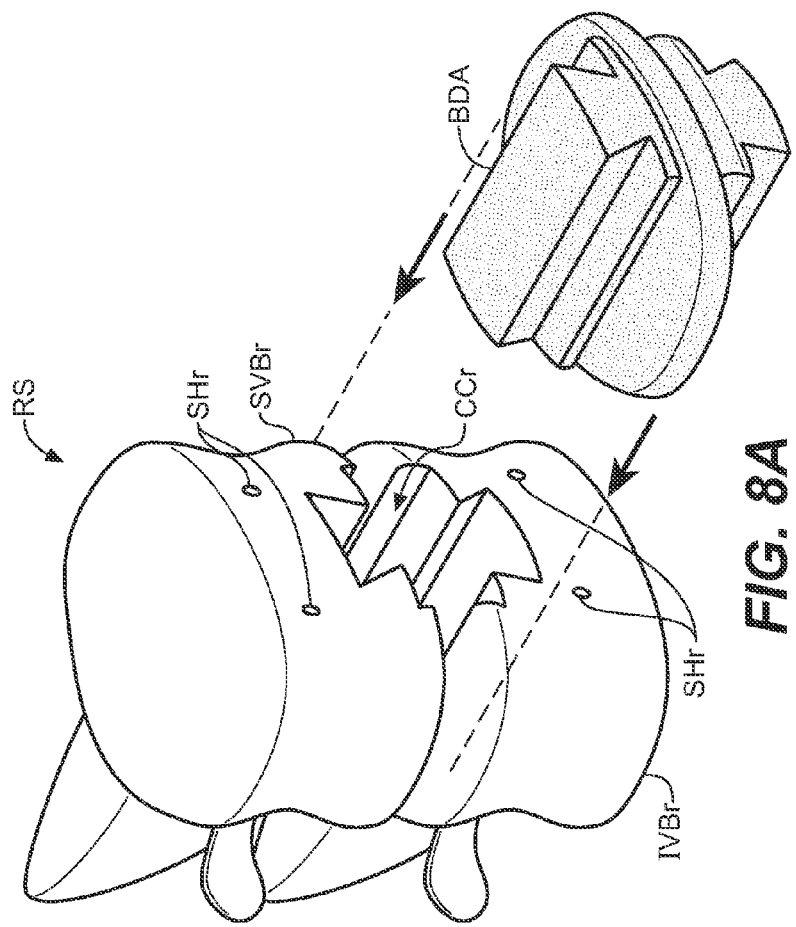
FIG. 8A is an upper rear perspective view showing the donor bone-disc-bone allograft poised for placement in the recipient patient spine.
Figure 9A:
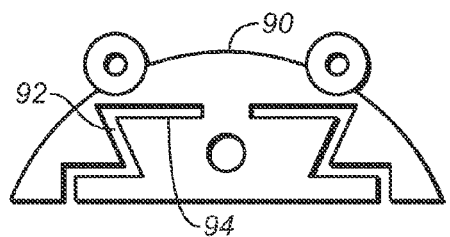
FIGS. 9A through 14B are top plan views showing six different pairs of donor and recipient cutting jigs with alternative cutting jig cut patterns, varied according to the specific anatomical location and biomechanical requirements.
Figure 10A:
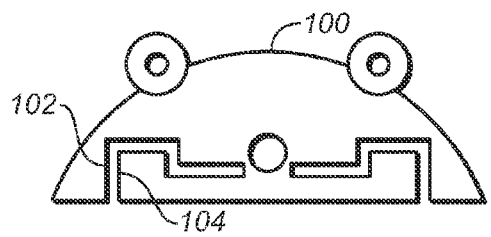
Figure 9B:
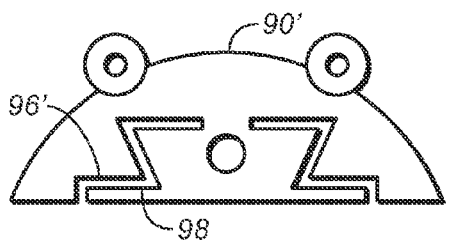
Figure 10B:
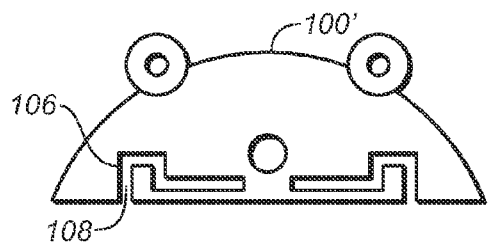
Figure 11A:
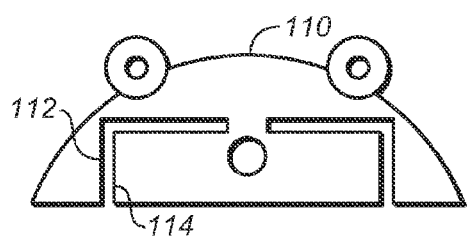
Figure 12A:
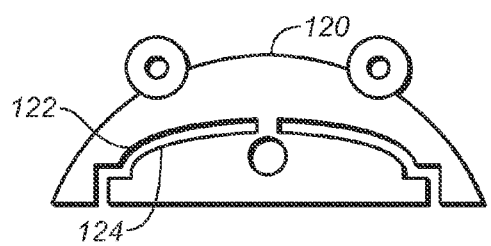
Figure 11B:
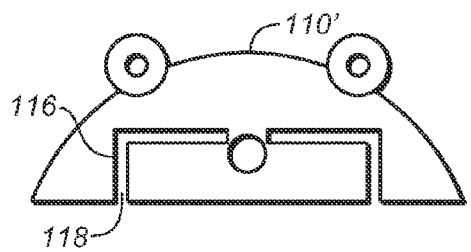
Figure 12B:
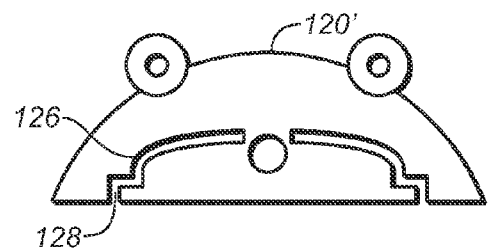

FIG. 8A shows the prepared portions of the recipient spine segment RS. As noted previously, the residual screw holes SHr and the contoured cavity CCr remain. FIG. 8B shows the recipient spinal segment after implantation of the allograft in the contoured cavities of the superior and inferior vertebral body of the recipient spine. The prepared portion of the superior vertebral body of the graft is placed in the contoured cavity in the recipient's superior vertebral body; the prepared portion of the inferior vertebral body of the graft is placed in the contoured cavity in the inferior vertebral body of the recipient; the healthy allograft intervertebral disc remains attached to the bone of the superior and inferior allograft end plates throughout this process. As will be appreciated, the shape of this exemplary donor allograft and the contoured cavity of the recipient resemble the joining method employed by dovetail tails and pins in woodworking. The principles for cutting, sizing, and fitting the elements are essentially identical.

Figure 13A:
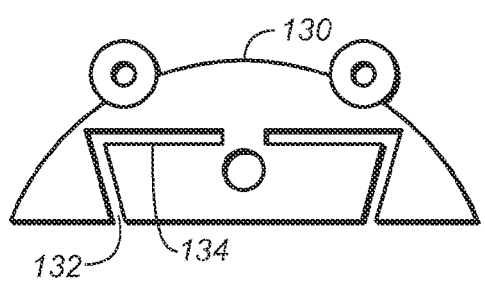
Figure 14A:
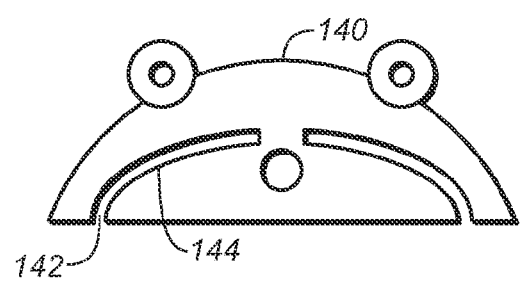
Figure 13B:
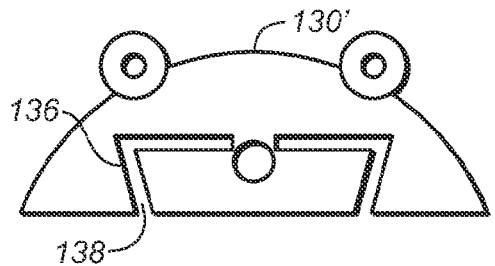
Figure 14B:
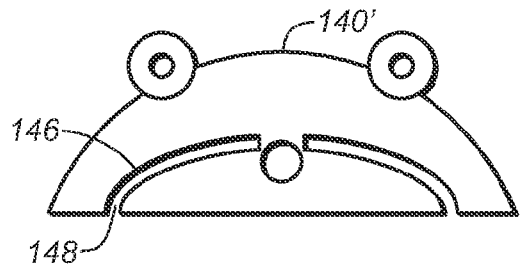

FIGS. 9A-12B show four different matched pairs of cutting jigs, respectively 9A-9B, 10A-10B, 11A-11B, and 12A-12B. These show that several suitable slot patterns may be employed for preparing the contoured cavity and the allograft, including, without limitation, an angled Z pattern, 9A-9B; a rectangular sled pattern 10A-10B; an L-shaped pattern 11A-11B; a rectangular/oval configuration 12A-12B, an oblique/horizontal configuration 13A-13B; and an oval configuration 14A-14B. As will be appreciated, such patterns may take a virtually unlimited number of practicable shapes, and all be used with both the disc measurement stylus and the allograft donor disc measurement ring to prepare the donor and recipient bone to matching size configurations for maximal contact and stability. As will be appreciated, in each pair of cutting jigs, the donor cutting jigs, 90 in FIG. 9A, 100 in FIG. 10A, 110 in FIG. 11A, 120 in FIG. 12A, 130 in FIG. 13A, and 140 in FIG. 14A, each have slots 92, 102, 112, 122, 132, 142, respectively, with an interior edge 94, 104, 114, 124, 134, 144, respectively, that trace or match the dimensions of the corresponding outer edge 96, 106, 116, 126, 136, and 146, respectively, of the cutting slot 98, 108, 118, 128, 138, 148, of the paired recipient cutting jig 90', 100', 110', 120', 130', 140'. In this way, the edges, angles, corners, and overall shape of the allograft is sized to match the prepared contoured cavity in the recipient spine.

While in general it is desirable that the slot patterns create both a contoured cavity and a matching allograft that are substantially bilaterally symmetrical along any medial line of symmetry (i.e., have reflection symmetry), other geometries, perhaps less than perfectly regular or symmetrical, are possible. Accordingly, the bilaterally symmetrical geometries described and shown herein shall not be considered as limiting.

The above disclosure is sufficient to enable one of ordinary skill in the art to practice the invention. The description also provides the best mode of practicing the invention presently contemplated by the inventor. However, while there is provided herein a full and complete disclosure of the preferred embodiments of this invention, the written description and the drawings do not limit the invention to the exact construction, dimensional relationships, and operation shown and described. Various modifications, alternative constructions, changes and equivalents will readily occur to those skilled in the art and may be employed, as suitable, without departing from the true spirit and scope of the invention.

Therefore, the above description and illustrations should not be construed as limiting the scope of the invention, which is defined instead by the appended claims.

What is claimed as invention is:

1. An apparatus for preparing vertebral body bone for osteochondral transplants of the vertebral disc between two prepared vertebral bodies, said apparatus comprising:

a first cutting assembly for preparing a contoured cavity in the anterior aspect of a recipient spinal segment, said contoured cavity extending from a portion of a superior vertebral body, through at least a portion of diseased intervertebral disc, and spanning into a portion of an inferior vertebral body, said first cutting assembly including a first cutting jig, a first indexing element disposed on or in said first cutting jig, and a disc measurement stylus; and a second cutting assembly for creating and harvesting a bone/disc combination allograft from a donor spinal segment, said bone/disc combination closely matching the contours of the contoured cavity so as to ensure a close press fit of the combination bone/disc allograft in the contoured cavity, said second cutting assembly including a second cutting jig and a donor alignment guide;

wherein said disc measurement stylus comprises two substantially parallel elongate blades, a connecting member joining said blades at one end, an indexing element support formed by or disposed on said connecting member, and a second indexing element disposed on said indexing element support, said second indexing element being the male or female counterpart to said first indexing element disposed on or in said first cutting jig, and wherein said blades are spaced apart so as to facilitate placement into the annulus fibrosis of the diseased disc on the surface of the bone end plate to establish the depth of bone removal from the vertebral bodies of the recipient spinal segment.

2. The apparatus of claim 1, wherein said first cutting jig includes a front side, a rear side, a top side, a bottom side, bone mounting elements for affixing said jig to the anterior aspect of a vertebrae in a recipient patient's spinal column, and cutting slots comprising at least one channel extending from said front side through said rear side for guiding the path of a cutting device and having outer and inner edges.

3. The apparatus of claim 1, wherein said second cutting jig includes a front side, a rear side, a top side, a bottom side, bone mounting elements for affixing said second cutting jig to the anterior aspect of a vertebral segment obtained from a cadaveric donor's spinal column, a first indexing element disposed on or in said second cutting jig, and cutting slots extending from said front side through said rear side for guiding the path of a cutting device, said cutting slots comprising at least one channel extending from said front side through said rear side for guiding the path of a cutting device and having inner edges that conform to the outer edges of the cutting slots in said first cutting jig; and a donor alignment guide.

4. The apparatus of claim 3, wherein said donor alignment guide comprises:

a frame defining an opening sized for placement over and around a donor spinal segment;

bosses disposed on said frame with fastener elements for affixing said frame to the donor spinal segment;

an indexing element support disposed on said frame; and a second indexing element disposed on said indexing element support, said second indexing element being the male or female counterpart to said first indexing element disposed on or in said second cutting jig.

5. The apparatus of claim 4, wherein said frame is an annulus.

6. The apparatus of claim 1, wherein said blades of said disc measurement stylus include a leading edge, an outer spine, an inner edge, an upper surface, a lower surface, and a heel portion.

7. The apparatus of claim 6, wherein said heel portions each include a bolster, and said connecting member joins said bolsters of each of said blades.

8. The apparatus of claim 7, wherein said connecting member includes an upper portion on which said indexing element support is formed.

9. The apparatus of claim 8, wherein said second indexing element is a male element and said first indexing element is a female element into which said second indexing element fits.

* * * * *